(12) United States Patent  
Burton et al.

(10) Patent No.: US 8,663,608 B2  
(45) Date of Patent: Mar. 4, 2014

(54) HYDROXYTYROSOL COMPOUNDS

(75) Inventors: Stephanie Gail Burton, Stellenbosch (ZA); Lester Merlin Davids, Noordhoek (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 13/497,483

(22) PCT Filed: Sep. 22, 2010

(86) PCT No.: PCT/IB2010/002373  
§ 371 (c)(1),  
(2), (4) Date: Jun. 20, 2012

(87) PCT Pub. No.: WO2011/036537  
PCT Pub. Date: Mar. 31, 2011

(65) Prior Publication Data  
US 2012/0269745 A1  Oct. 25, 2012

(30) Foreign Application Priority Data  
Sep. 22, 2009  (ZA) .................. 2009/06592

(51) Int. Cl.  
*A61Q 17/04* (2006.01)  
*A61K 31/55* (2006.01)  
*A61K 31/45* (2006.01)

(52) U.S. Cl.  
USPC ............................. 424/59; 514/730; 514/738

(58) Field of Classification Search  
USPC .............................. 424/59; 514/738, 731, 730  
See application file for complete search history.

(56) References Cited

U.S. PATENT DOCUMENTS

| | | | |
|---|---|---|---|
| 6,437,004 B1 | 8/2002 | Perricone | |
| 2004/0137129 A1 | 7/2004 | Zhao et al. | |

OTHER PUBLICATIONS

Mattinen et al., FEBS Journal, 2005, 272, 3640-3650.*  
Celano et al., "Reduced Toxicity of Olive Mill Waste Waters by Oxidative Coupling with Biomimetic Catalysis," *Environmental Science & Technology*., 2008, vol. 42, No. 13, pp. 4896-4901.

Di Maio et al., "HPLC-ESI-MS Investigation of Tyrosol and Hydroxytyrosol Oxidation Products in Virgin Olive Oil," *Food Chemistry*, 2011, vol. 125, pp. 21-28.  
De Lucia et al., "Oxidative Chemistry of the Natural Antioxidant Hydroxytyrosol: Hydrogen Peroxide-Dependent Hydroxylation and Hydroxyquinone/*O*-Quinone Coupling Pathways," *Tetrahedron*, 2006, vol. 62, pp. 1273-1278.  
Fernandez-Bolanos et al., "Hydroxytyrosol and Derivatives: Isolation, Synthesis, and Biological Properties," *Current Organic Chemistry*, 2008, vol. 12, pp. 442-463.  
Roche et al., "Antioxidant Activity of Olive Phenols: Mechanistic Investigation and Characterisation of Oxidation Products by Mass Spectrometry," *Journal of Royal Society of Chemistry*, 2005, published on Dec. 21, 2004 on http://ubs.rsc.org.  
Brigante et al., "Synthesis of Dimeric Phenylethanoids Isolated From olive oil Mill Wastewaters," *Natural Product Research*, 2006, pp. 792-797, vol. 20, No. 9.  
Dellagreca et al. "Low-Molecular-Weight Components of Olive Oil Mill Waste-Waters," *Phytochemical Analysis*, 2004, pp. 184-188, vol. 15, No. 3.  
Dellagreca et al. "Phenolic Components of Olive Mill Waste-Waters," *Natural Product Letters*, 2000, pp. 429-434, vol. 14, No. 6.  
Celano et al., "Reduced Toxicity of Olive mill Waste Waters by Oxidative Coupling with Biomimetic Catalysis," *Environmental Science & Technology*, 2008, pp. 4896-4901, vol. 42, No. 13.

* cited by examiner

*Primary Examiner* — Blessing M Fubara  
*Assistant Examiner* — Kauser M Akhoon  
(74) *Attorney, Agent, or Firm* — Womble Carlyle Sandridge & Rice, LLP

(57) ABSTRACT

A hydroxytyrosol polymer formed by either C—C coupling or C—O—C coupling is provided. Preferred polymers are formed by C—C coupling and the dimer has the following structure:

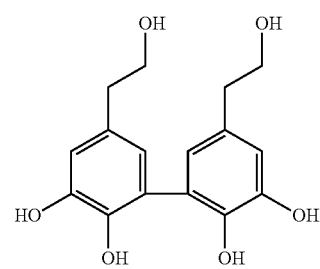

Compounds of the invention have been found to have antioxidant properties and their use in antioxidant compositions forms a further aspect of the invention.

6 Claims, 12 Drawing Sheets

FIGURE 8.1
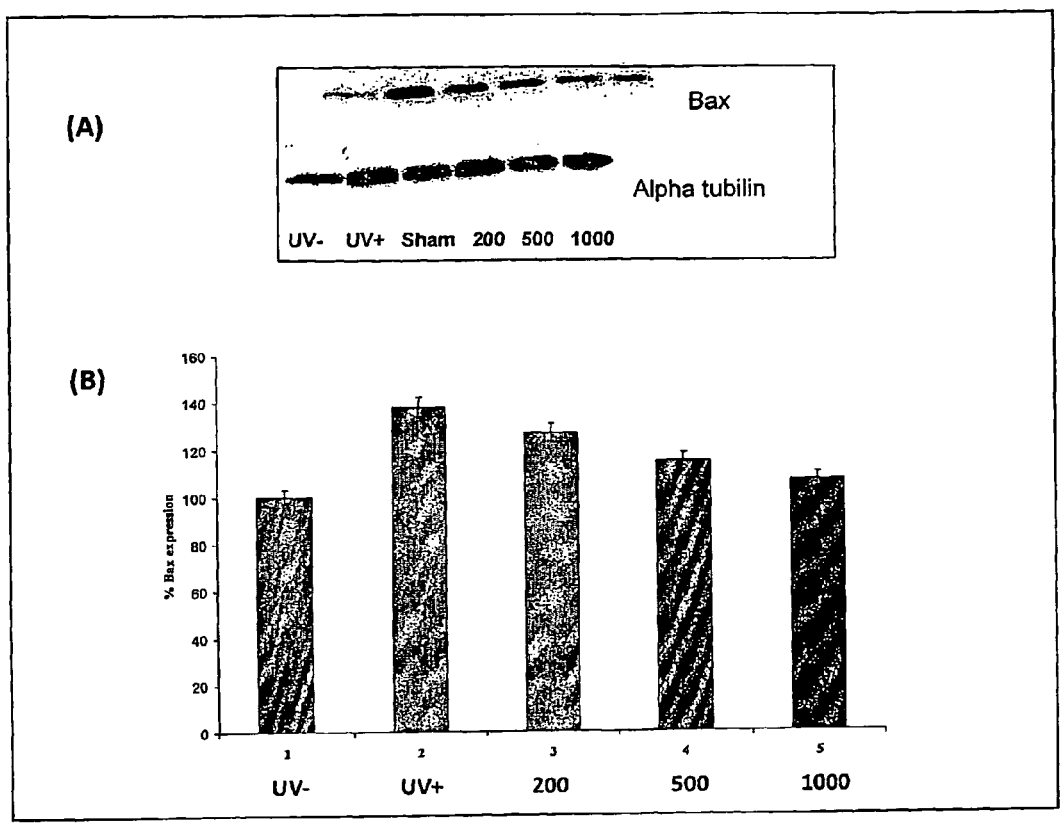

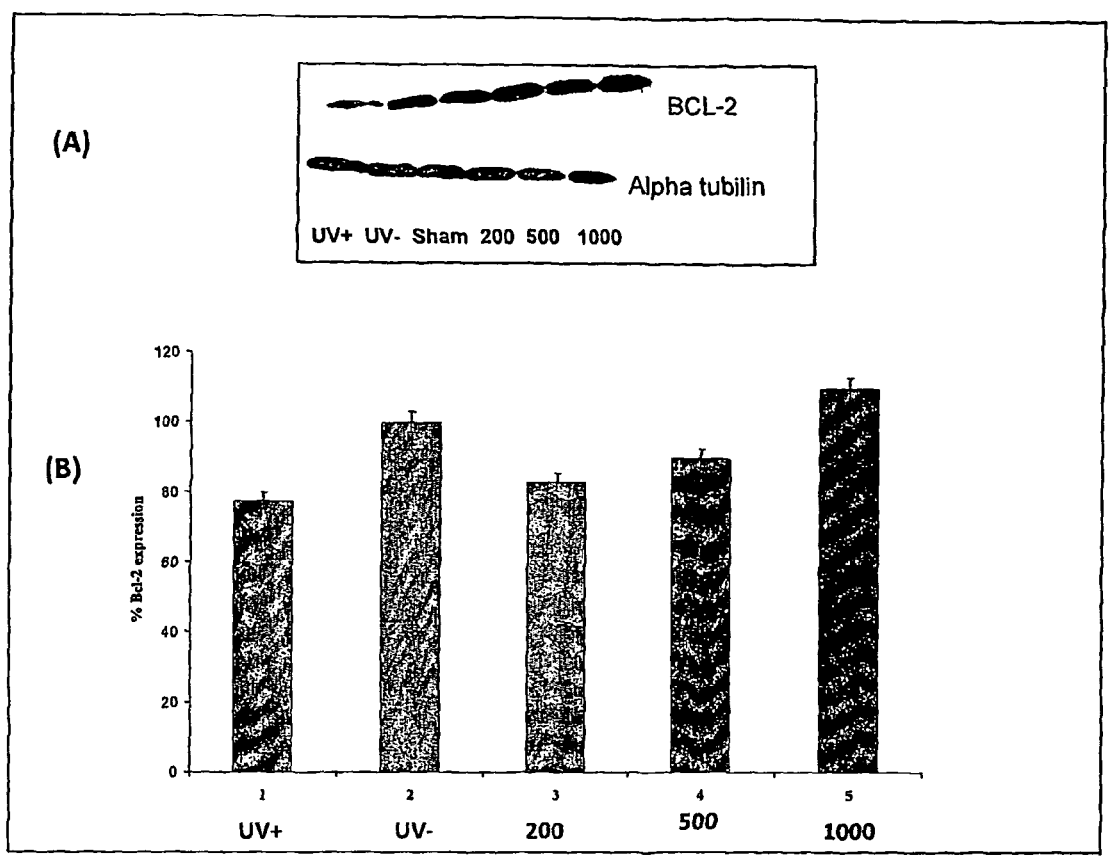
FIGURE 8.2

FIGURE 8.3
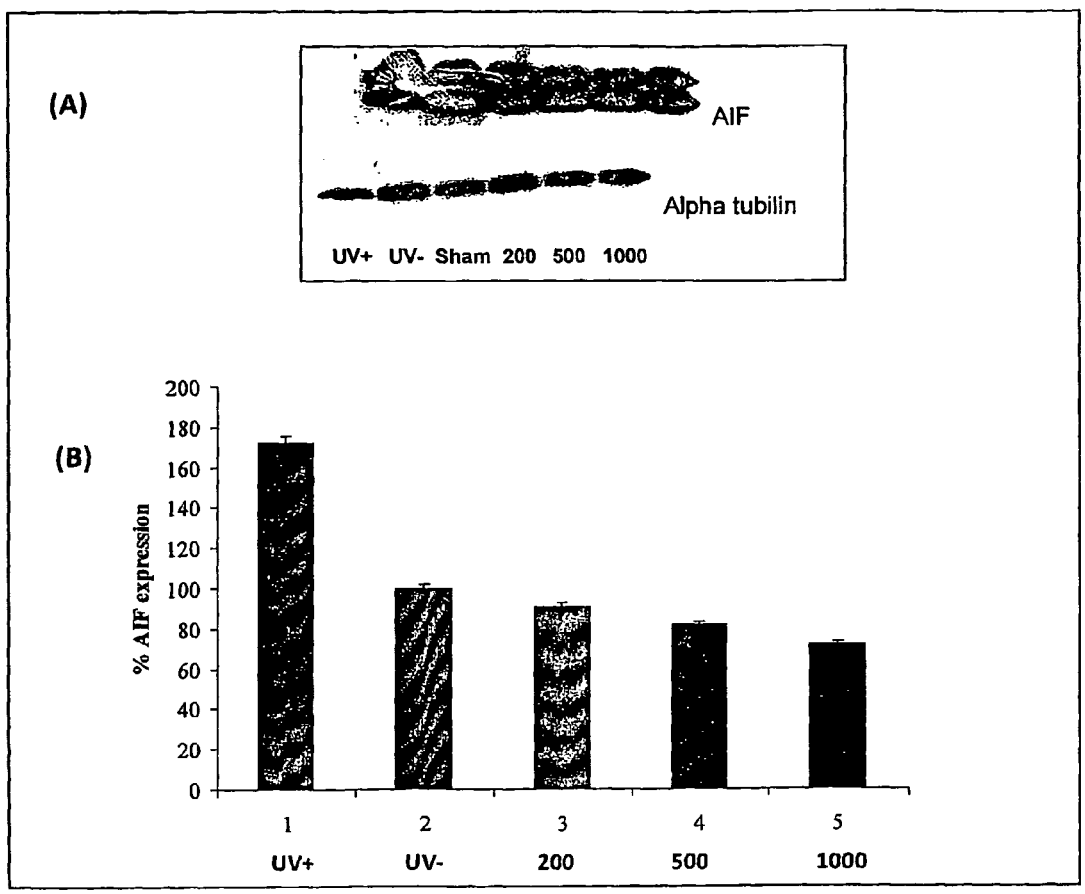

FIGURE 8.4
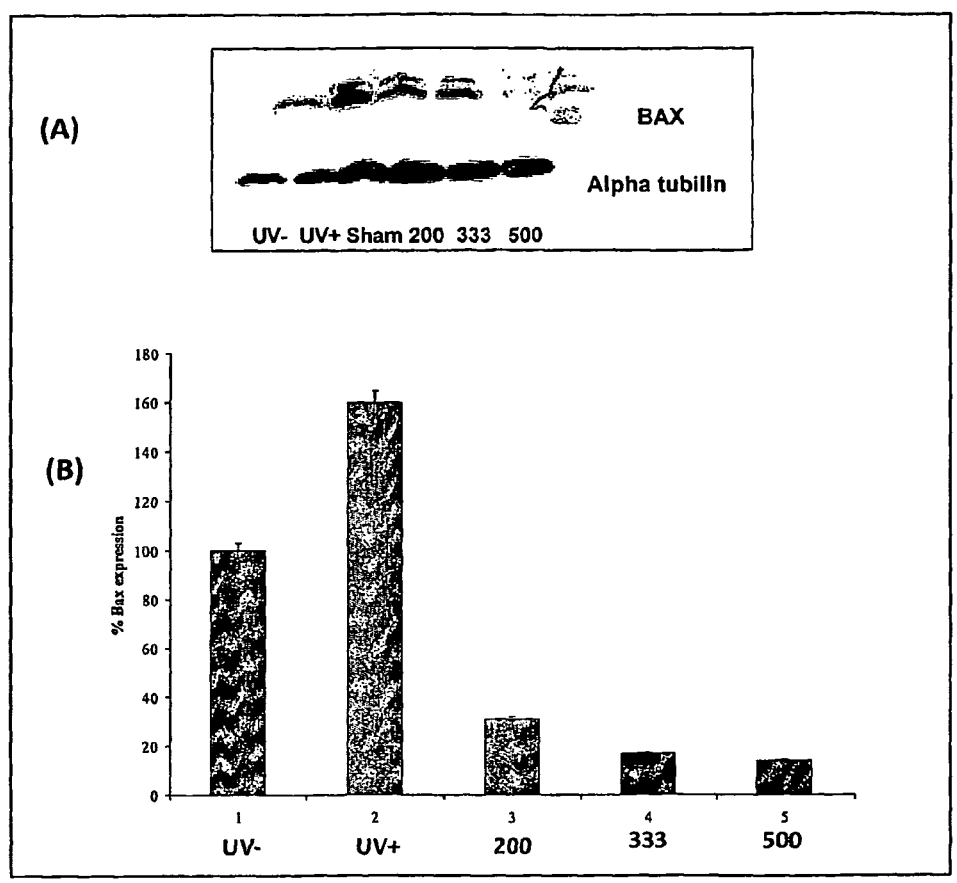

FIGURE 8.5
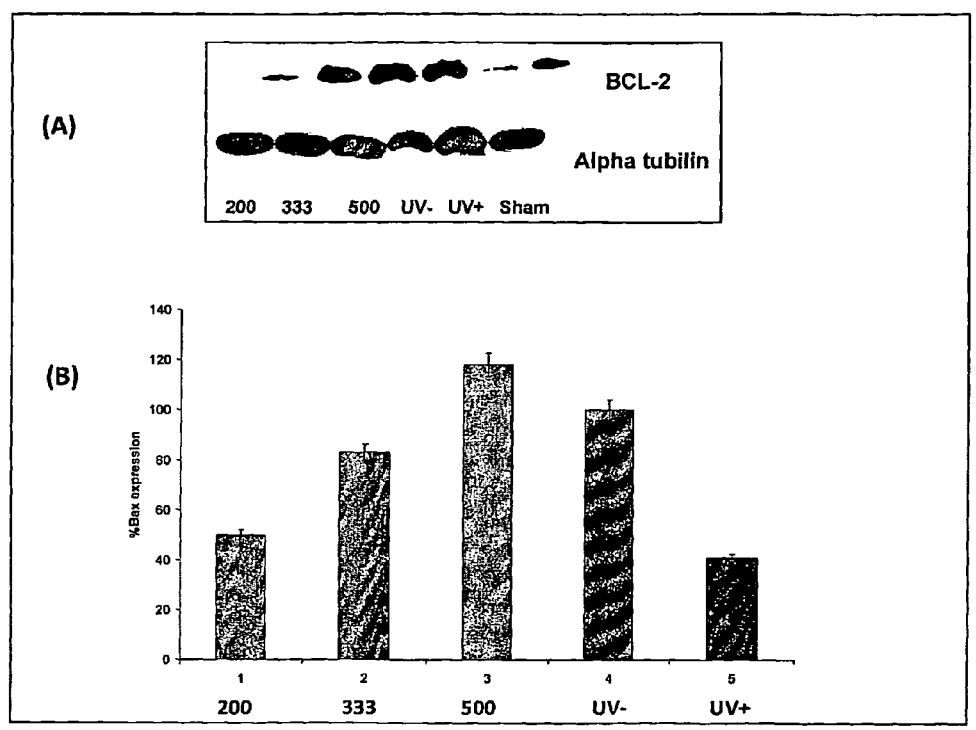

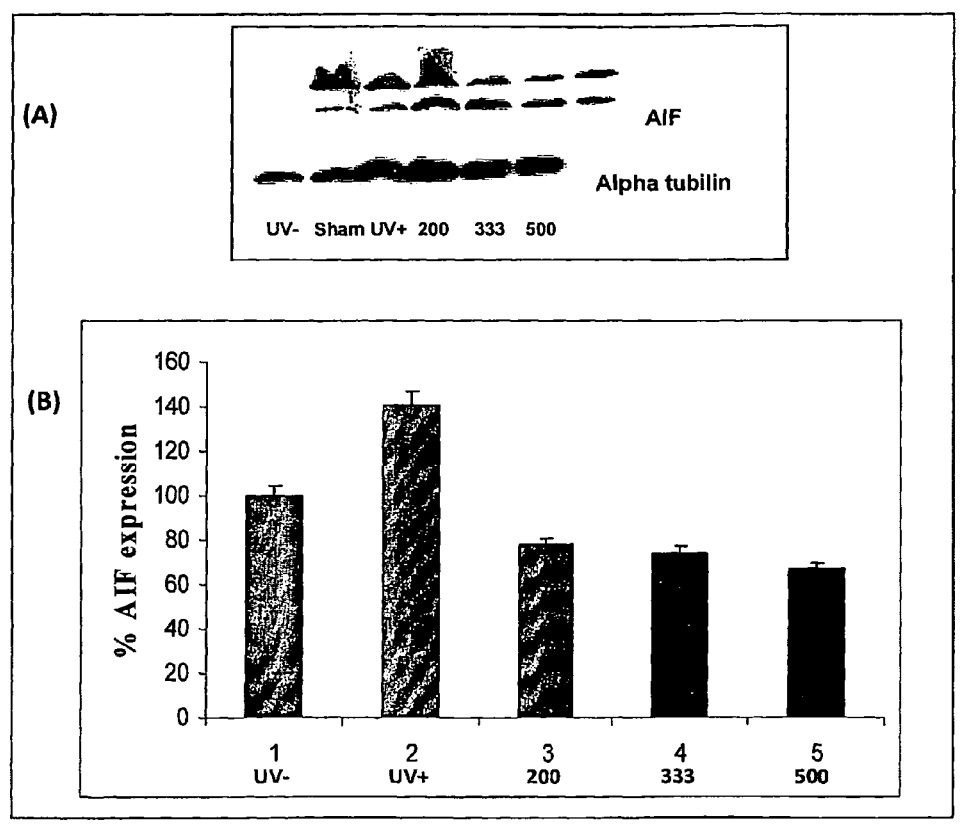
FIGURE 8.6

Figure 9.1
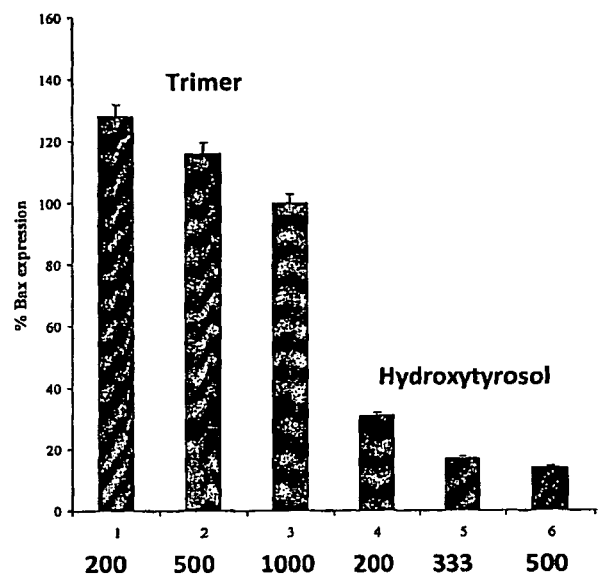
Figure 9.2
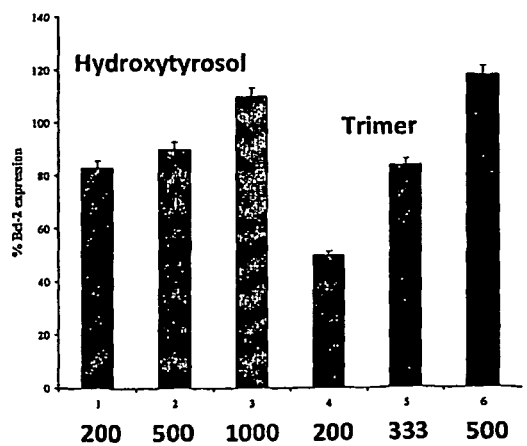

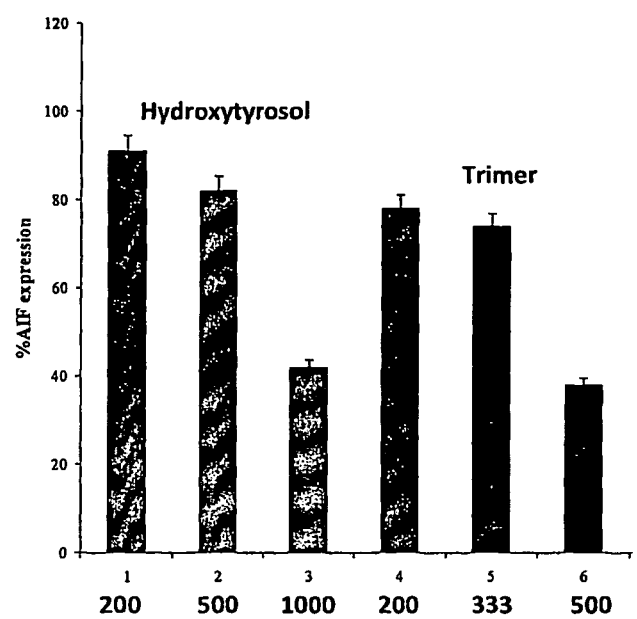
Figure 9.3

HYDROXYTYROSOL COMPOUNDS

FIELD OF THE INVENTION

This invention relates to compounds derived from hydroxytyrosol and to their use in antioxidant compositions.

BACKGROUND TO THE INVENTION

Hydroxytyrosol is a phytochemical with powerful antioxidant properties. It is found in olive oil in the form of its elenolic acid ester oleuropein and in its plain form. Hydroxytyrosol is available commercially at a feasible price, and can be produced using an enzymatic reaction or extracted.

OBJECT OF THE INVENTION

It is an object of this invention to provide new hydroxytyrosol derived compounds, and particularly compounds having antioxidant properties superior to hydroxytyrosol.

SUMMARY OF THE INVENTION

In accordance with this invention there is provided a hydroxytyrosol polymer formed by either C—C coupling or C—O—C coupling.

Further features of the invention provide for the polymer to be one or more of a dimer, trimer and a higher oligomer; for the polymer to preferably be formed by C—C coupling; for the dimer to have the following structure:

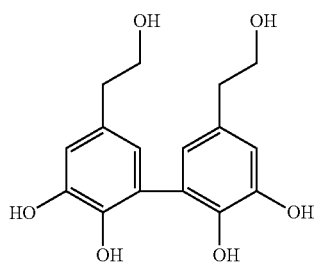 [SMILES: OCCc1cc(O)c(O)c(-c2cc(CCO)cc(O)c2O)c1]

and for trimer to have the following structure:

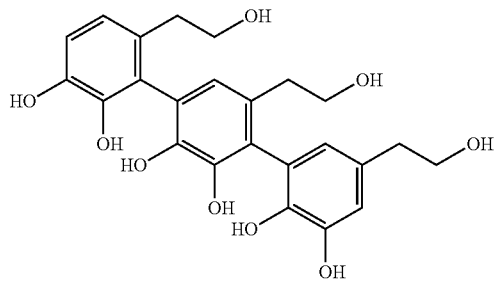

The invention also provides an antioxidant composition which includes a hydroxytyrosol polymer.

Further features of the invention provide for the polymer to be formed by C—C coupling; for the polymer to be one or more of a hydroxytyrosol dimer, hydroxytyrosol trimer and an hydroxytyrosol oligomer; for the dimer and the trimer to preferably have the structures defined above; for the composition to be suitable for use on skin, for the composition to be in the form of a cream, lotion or spray; for the composition to be suitable for use on human or animal skin; alternately for the composition to be a medicament, and for the medicament to include one or more other active ingredients or excipients.

The invention still further provides for the use of a hydroxytyrosol polymer as an antioxidant.

Further features of the invention provide for the polymer to be formed by C—C coupling; for the polymer to be a dimer, trimer or oligomer; for the dimer and trimer to preferably have the structure defined above; for the use of hydroxytyrosol dimer as a UV protectant in compositions suitable for use on skin; alternately in a medicament; for the medicament to include any other suitable active ingredients and excipients; and for the medicament to be to be in the form of parenterals or non-parenterals, particularly tablets and capsules The invention yet further provides a process for preparing a hydroxytyrosol polymer which includes polymerizing hydroxytyrosol using laccase as a catalyst.

Further features of the invention provide for the use of a reaction medium containing water-miscible organic solvents such as acetone, methanol or ethanol, or water-immiscible solvents such as ethyl acetate, at percentages (volume for volume) ranging from 10% to 70% with aqueous buffer.

Still further features of the invention provide for the use of a range of substrate concentration ratios (relative to the amount of laccase present) from 50 U laccase:1 g hydroxytyrosol to 1000 U laccase: 1 g hydroxytyrosol; and for the use of laccase in a free or immobilised form.

BRIEF DESCRIPTION OF THE DRAWINGS

The invention will be described, by way of example only, with reference to the drawings in which:

FIG. 8.1 is a depiction of the Western blot results to determine the effect of hydroxytyrosol on Bax expression;

FIG. 8.2 is a depiction of the Western blot results to determine the effect of hydroxytyrosol on Bcl-2 expression;

FIG. 8.3 is a depiction of the Western blot results to determine the effect of hydroxytyrosol on AIF expression;

FIG. 8.4 is a depiction of the Western blot results to determine the effect of the Polymer Compound 57 on Bax expression;

FIG. 8.5 is a depiction of the Western blot results to determine the effect of the Polymer Compound 57 on Bcl-2 expression;

FIG. 8.6 is a depiction of the Western blot results to determine the effect of the Polymer Compound 57 on AIF expression;

FIG. 9.1 is a bar graph illustrating an analysis of the Western blot results to determine the effect of the antioxidants on Bax expression;

FIG. 9.2 is a bar graph illustrating an analysis of the Western blot results to determine the effect of the antioxidants on Bcl-2 expression; and FIG. 9.3 is a bar graph illustrating an analysis of the Western blot results to determine the effect of the antioxidants on AIF expression.

DETAILED DESCRIPTION WITH REFERENCE TO THE DRAWINGS

The invention provides a polymer formed from hydroxytyrosol monomers. The polymers can be formed by either C—C coupling or C—O—C coupling, as described in more detail below, and can be produced by oxidation of hydroxytyrosol using laccase.

Figure 1:
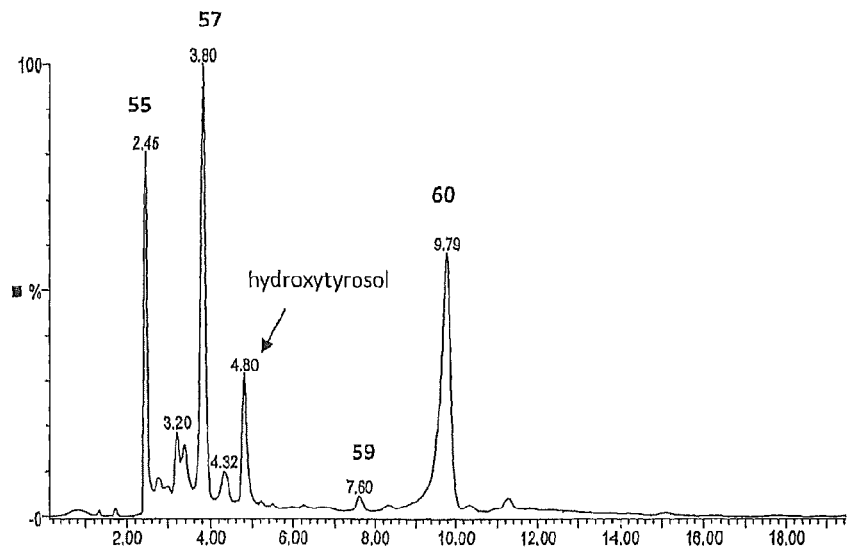
FIG. 1 is an HPLC profile showing bioconversion of hydroxytrosol by laccase obtained *T. pubescens* in 20% methanol.
Figure 2:
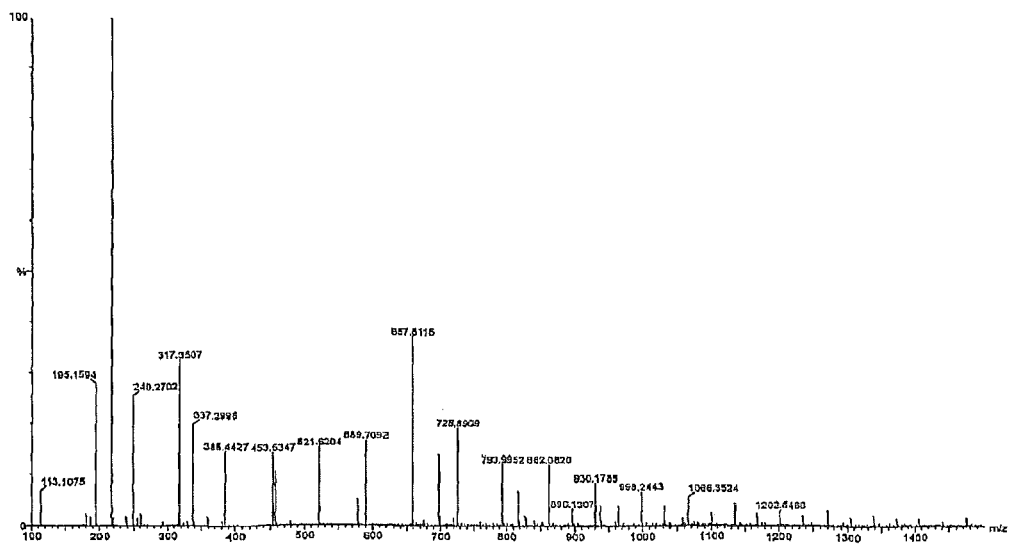
FIG. 2 is an LC-MS profile of product 55 in FIG. 1, indicating the presence of a polymer obtained from bioconversion of hydroxytyrosol by laccase in reaction medium containing 20% methanol.

According to one embodiment, hydroxytyrosol, synthesized using tyrosinase as a biocatalyst, and then purified initially by preparative TLC plate was oxidized by laccase obtained from $T.\ pubescens$, in sodium acetate buffer medium containing 20% methanol. The reaction was monitored by HPLC as shown in FIG. 1. After 6 h, 80% conversion of hydroxytyrosol (represented by the peak with retention time 4.8 min) was achieved, and 6 product peaks were observed. These peaks represented various products of the hydroxytyrosol-laccase reaction.

The identification of the new product peaks was achieved using LC-MS as shown in FIGS. 2 to 5. A product with retention time 2.45 min was denoted polymeric product 55 and its LC-MS profile shown in FIG. 2. Product 55, constituting 27% of the total peak area, comprised 8 monomers (1202.5 m/z) of hydroxytyrosol. These are linked either by C—C bonds or C—O bonds.

Figure 3:
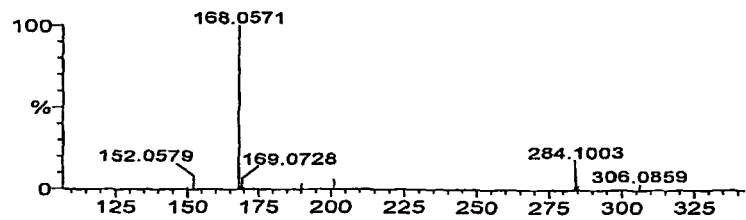
FIG. 3 is an LC-MS profile of product 57 in FIG. 1, indicating the presence of a dimeric product (mass 306) obtained from bioconversion of hydroxytyrosol by laccase in reaction medium containing 20% methanol.

A product with retention 3.8 min was denoted product 57 and constituted 39% of the total peak area. Its LC-MS profile is shown in FIG. 3 and it was found to contain 2 monomers (306.08 m/z) of hydroxytyrosol, thus forming a dimeric product.

Figure 4:
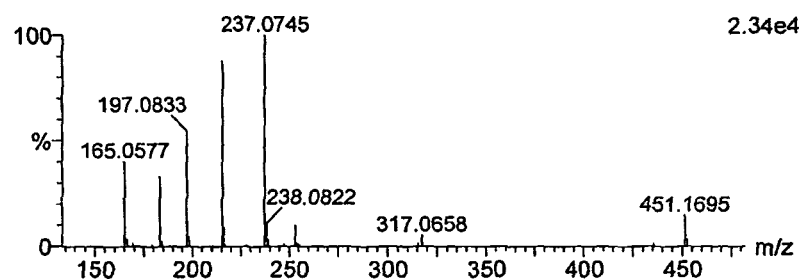
FIG. 4 is an LC-MS profile of product 59 in FIG. 1 with retention time 7.60 min, indicating the presence of oligomeric compounds obtained from bioconversion of hydroxytyrosol by laccase in reaction medium containing 20% methanol.
Figure 5:
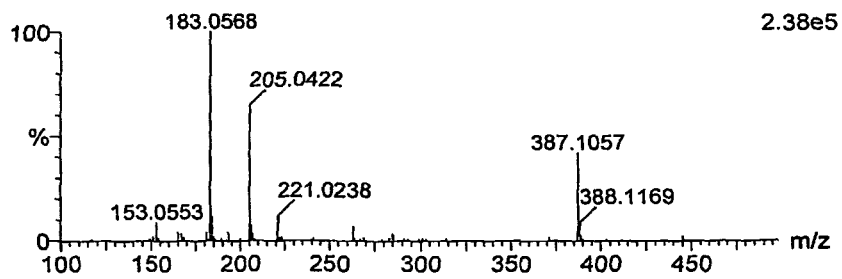
FIG. 5 is an LC-MS profile of product 60 in FIG. 1 with retention time 9.79 min, indicating the presence of oligomeric compounds obtained from bioconversion of hydroxytyrosol by laccase in reaction medium containing 20% methanol.

A product with retention 7.6 min was denoted product 59 and constituted 1% of the total peak area. The LC-MS profile of product 59 is shown in FIG. 4. A product with retention time 9.79 min, constituting 20% of the total peak area, was denoted product 60 and its LC-MS profile shown in FIG. 5. Both product 59 and product 60 appear to be oligomeric products of hydroxytyrosol.

The choice of organic solvent influences the selectivity of the hydroxytyrosol-laccase reactions. This is illustrated by conducting the oxidation of hydroxytyrosol by laccase in sodium acetate reaction medium containing 50% acetone, 50% methanol or 50% ethyl acetate (biphasic system). Table 1 shows the HPLC detected results of various reaction mixtures. From the results it will be apparent that the nature of the polymeric product produced by the reaction differs based on the type of organic solvents used.

As shown in Table 1, a dimer of hydroxytyrosol, product 57, is the main product with a 52% yield in a reaction mixture containing 50% acetone. Yields of the other products (55, 59 and 60) from the same reaction mixture are very low at about 3%.

For reaction medium containing 50% methanol, the main polymer obtained is product 59, and for the reaction mixture containing ethyl acetate, product 60 is the main polymer produced.

It is notable that the intensity of the peak representing the polymeric product 55 in reaction mixtures containing acetone, ethyl acetate or 50% methanol, is decreased significantly as compared to the same peak in the reaction containing 20% methanol.

TABLE 1

Conversions of hydroxytyrosol by laccase detected by HPLC in the presence of each cosolvent after 6 h.

| Organic solvent* | Hydroxytyrosol conversion based on the HPLC peak area comparison (%) | Hydroxytyrosol not reacted (%) | Product 55 (%)* | Product 57 (%) | Product 59 (%) | Product 60 (%) |
|---|---|---|---|---|---|---|
| Acetone 50% | 60 | 40 | 3 | 52 | 3 | 3 |
| Methanol 50% | 96 | 4 | 3 | 18 | 69 | 2 |
| Ethyl acetate 50% | 95 | 5 | 3 | 0.5 | 1 | 50 |

*used as cosolvent with sodium acetate buffer (0.1M, pH 5)

**determined on the basis of HPLC peak areas.

Figure 6:
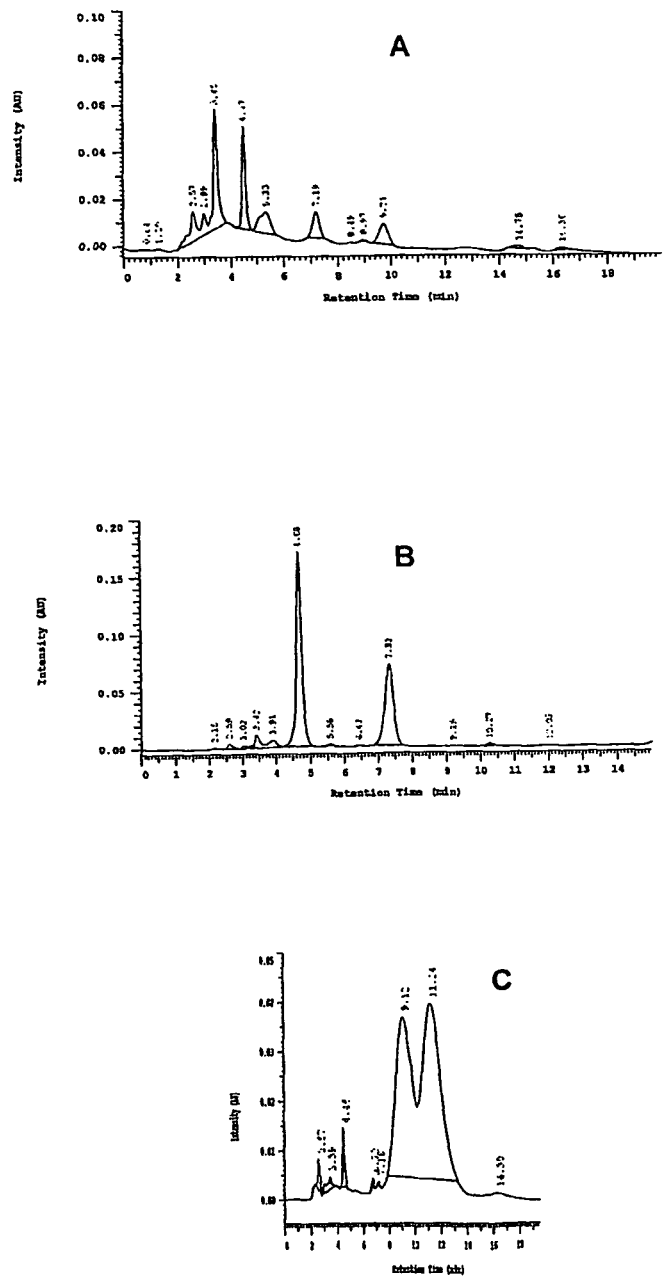
FIG. 6 shows HPLC profiles indicating bioconversion of hydroxytrosol by laccase, A: reaction medium containing 50% acetone, the main product is a dimer, retention time 3.40 min; B: reaction medium containing 50% methanol, the main product is product 59, retention time 7.33 min and C: the reaction medium containing 50% ethyl acetate, the main product is product 60 represented by a peak with retention time 9.12 min.

Polymeric product formation is found to decrease with an increase in the amount of organic solvent in the reaction medium. This is attributed to the fact that organic solvents decrease the hydrophobic interaction of molecules in solution. Thus, the results obtained clearly show that organic solvents have an influence on the nature of hydroxytyrosol-laccase reaction products. The HPLC profiles indicating bioconversion of hydroxytrosol by laccase are shown in FIG. 6 and a summary of the hydroxytrosol-laccase reaction products is provided in Table 2.

TABLE 2

Summary of the products of hydroxytyrosol-laccase reactions

| Laccase substrate | Organic solvent* | Product |
| --- | --- | --- |
| Hydroxytyrosol | 50% acetone | Major product was a dimer with molecular weight of 306 m/z |
| Hydroxytyrosol | 50% ethyl acetate | Major product was an unknown product 60 |
| Hydroxytyrosol | 50% methanol | Major product was an unknown product 59 |

*used as cosolvent with sodium acetate buffer (0.1M, pH 5)

As indicated above, hydroxytyrosol reactions are strongly affected by the use of organic solvents. The ability to control polymerisation in the hydroxytyrosol-laccase reactions could be attributed to the structure of the compound. The difference between tyrosol and hydroxytyrosol is an increased polarity/hydrophilic nature as well as increased steric size in hydroxytyrosol. Although increased polarity of a compound could result in more reactivity, this effect could be nullified by increased steric hindrance and decreased hydrophobic interactions effected by organic solvents. For instance, hydroxylation of tyrosol near the para-hydroxyl group might result in some steric hindrance, in that two hydroxytyrosol radicals couple to form a dimeric structure, but due to spatial limitation in this dimer it could be sterically difficult to attach more radicals. Thus, the steric effects in conjunction with the effects of organic solvents, that is decreasing the hydrophobic interactions of molecules, in the reaction medium might have resulted in the production of low molecular weight compounds. Besides steric and hydrophobic interaction effects, the ability to control polymerization of hydroxytyrosol could also be attributed to that fact that (a) the hydroxyl group could alter the delocalization of the unpaired electrons in the radical intermediate and hence, possibly, stabilize the radical and lead to lower molecular weight products, or (b) the radical intermediates of tyrosol and hydroxytyrosol could also interact differently with the organic solvents therefore resulting into different products.

The presence of the additional hydroxyl group in hydroxytyrosol has a profound effect in that reactions of hydroxytyrosol with laccase are more controllable as compared to tyrosol-laccase reactions. The high reactivity of tyrosol as attributed to its structural configuration is consistent with many laccase polymerization reactions reported in the prior art. Thus, the inference can be made that the structural configuration of laccase substrates has an influence on the reactivity of the radicals generated. Furthermore, the interactions of these radicals in the reaction medium can be influenced by nature of organic solvents used. This demonstrates that the reaction medium can be engineered or manipulated for the purpose of selecting the desired polymer product. The means that the desired polymer product can be selectively produced and a purification process optimized.

Of the polymers of hydroxytyrosol, the dimer and trimer form a specific focus of this invention. These will be referred to hereafter as "the dimer" or the "dimeric compound" and the "the trimer" or "the trimeric compound" respectively. Both the dimer and the trimer can be formed by either C—C coupling or C—O—C coupling. It is specifically the dimer and the trimer formed by C—C coupling that are of particular relevance to the present invention and the structures of these are at present thought to be the following:

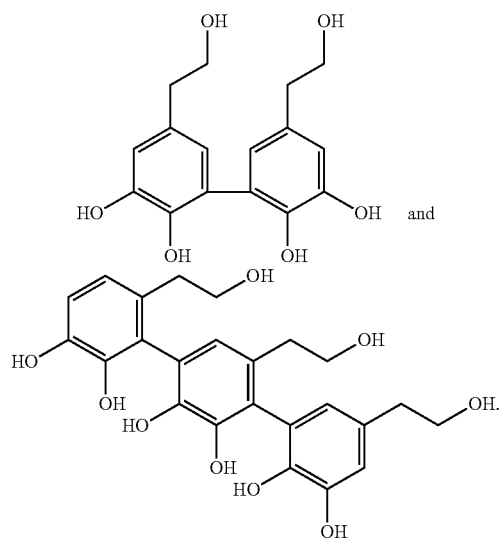

As indicated above, both the dimeric and the trimeric compound are produced by the polymerization of hydroxytyrosol in a reaction catalysed by the biocatalyst laccase, dependent on reaction conditions including variation of organic solvent: aqueous buffer ratio and ratio of substrate to enzyme. The examples below further illustrate the process.

Oxidation of Hydroxytyrosol by Laccase to Yield Polymer

Laccase (80 U) and hydroxytyrosol (1 g) were added to sodium acetate buffer (pH 5, 0.1M, 200 ml) and methanol (200 ml). The reaction was covered with foil and shaken at 180 rpm; 30° C. Samples were periodically taken and analyzed with the HPLC. The mobile phase used for HPLC analysis was methanol:acetic acid:$H_2O$ (20:2.5:80) with a flow rate 1 ml/min, using a 018 Waters (250 mm×4.6 nm) reverse phase column and UV detection at 280 nm. Peaks were analyzed using HPLC Manager, Merck Hitachi model D 700 data software. The percentage conversion was obtained by comparing the peak area of reaction sample with that of a control. The products of the reaction were monitored by TLC analysis with eluent toluene: ethyl acetate: formic acid solution (5:4:1).

An equal amount of ethyl acetate to the reaction mixture was used to recover the organic product from the reaction mixture. The mixture was shaken vigorously following which the mixtures were allowed to separate. The organic part was recovered and dried using the rotor evaporator and then re-suspended in methanol. The sample was purified using flash chromatography (eluent, toluene: ethyl acetate: formic acid solution (5:4:1)). The purified product was again recovered using the rotor evaporator and a sample was dissolved in d-chloroform for $^1$H-NMR analysis. $^1$H-NMR was conducted with d-chloroform at 300 MHz.

The product 57, hereinafter referred to as Polymer Compound 57, obtained has an Rf value of 0.3 on TLC and a molecular weight 306 by MS. The proposed possible structures for the dimer and the trimer are shown below:

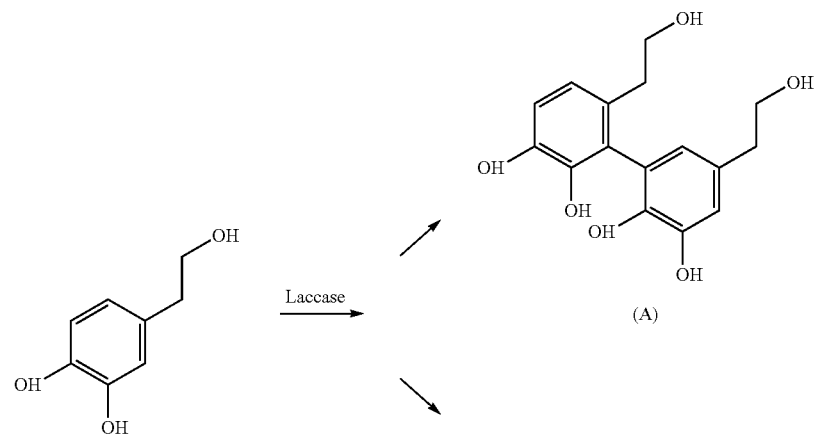
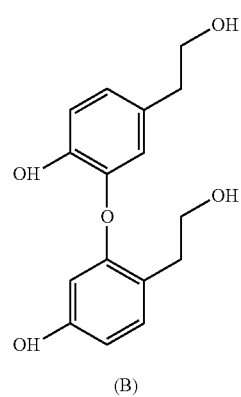
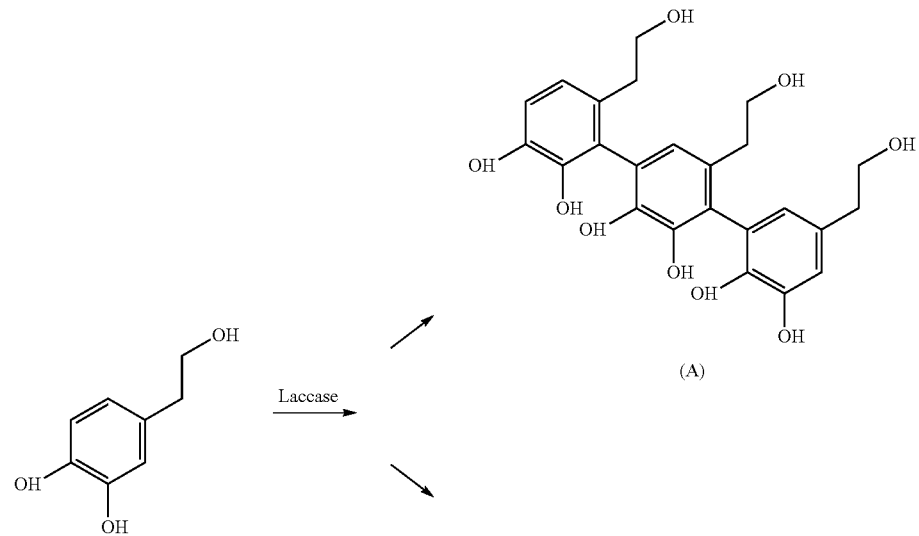

-continued

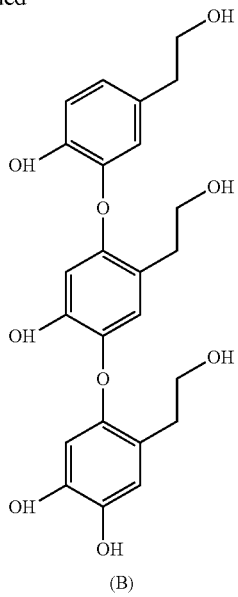

(B)

The products can be explained through consideration of the coupling reaction involved. Under basic conditions, phenoxy radical coupling leads to a C—O—C coupling (product B), while under acidic conditions it leads to a C—C coupling (product A). Under neutral conditions (using a buffer) both of these coupling reactions have 50% chance of occurring. Both coupling methods are thus provided here.

However, it has been noted that the C—C linked dimer and trimer appear to exhibit significantly more antioxidant activity than the C—O—C linked dimer and trimer and it is the C—C linked Polymer Compound 57 that was used in the following antioxidant assays.

Further Analysis: Oxidation of the Substrates by Laccase

In a second reaction, the reaction mixture contained hydroxytyrosol (≈0.002 g in 4 ml methanol), sodium acetate buffer pH 5.0 (4 ml) and laccase (1.6 U). The reaction was carried out for 14 h at 30° C. while shaking at 180 rpm using an orbital shaker. The oxidation products were analysed by HPLC and LC-MS.

HPLC Analysis of Oxidation Products

An equal volume of ethyl acetate was added to the reaction mixture to recover the organic phase from the mixture. The mixture was shaken vigorously and then allowed to stand and separate and the organic phase was recovered and analysed on a Merck-Hitachi LaChrom HPLC system (Merck, Germany) equipped with an L7100 pump, a P-7200 autosampler and an L-7400 UV detector. Identification and quantitative determination of products was done by reversed phase HPLC, on a PFP(2) column (LUNA 250×4.60 mm, 5 µm, Phenomenex, Germany) using acetonitrile, 0.1% acetic acid and deionized water (20:2.5:80) as solvent with isocratic elution at a flow rate of 1 mlmin$^{-1}$ and an oven temperature of 25° C.

LC-MS Analysis of Oxidation Products

LC-MS was performed on a Waters Acquity UPLC system equipped with a binary solvent manager and autosampler coupled to a Waters Ultima ESI Q-TOF mass spectrometer. The products were first separated using the isocratic conditions described above (except that 0.1% formic acid was used instead of 0.1% acetic acid) and a linear gradient as follows: 95% solvent A and 5% solvent B (0-2 min), 20% A and 80% B (2-25 min), 100% B (25-30 min), and 95% A and 5% B (30-40 min), where solvent A is 0.1% formic acid and solvent B is acetonitrile. The mass spectrometer was operated in negative ionization mode with a capillary voltage of –3.7 kV and a cone voltage of 35 V. The source temperature was 120° C. and disolvation temperature was 370° C. The desolvation and cone gas flows (both $N_2$) were 370 L/h and 50 L/h, respectively. Masses were scanned from 150-1450 amu and data were collected and processed using MassLynx v. 4.0 software (Waters). The instrument was calibrated using a NaF solution.

LC-MS results showed dominant signals at m/z 303.2, $t_R$=13.97 min (oxidized dimer; [M]=304); m/z 309.2, $t_R$ 26.00 (dimer, [M]=308), and m/z 353.2, $t_R$ 25.71 (formic acid adduct). The hydroxyl group on the benzene ring is ortho or para directing and molecules with a free C-5 position usually dimerize through 5-5 linkages due to stability of C—C bonds and low heat of formation of 5-5 linkages when compared to ether linkages. In addition, the hydroxytyrosol structure resembles lignin monomers which are known to form oligomers through 5-5 and 4-O-5 linkages. Considering these facts and LC-MS results the structure of the polymer was determined to be the following:

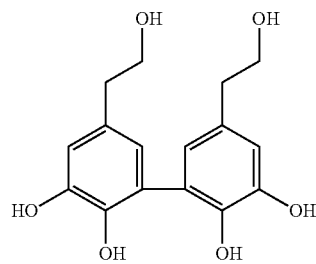 [SMILES: OCCc1cc(O)c(O)c(-c2cc(CCO)cc(O)c2O)c1]

5,5'-bis(2-hydroxyethyl)-[1,1'-biphenyl]-2,2',3,3'-tetraol
m/z: 306.11 (100.0%), 307.11 (17.5%). 308.12 (1.5%), 308.11 (1.2%)

Antioxidant Assays to Measure Antioxidant Activity

The antioxidant activity of the hydroxytrosol polymers can be measured by using in vitro antioxidant assays. Three different antioxidant assays were used to give an indication of Polymer Compound 57's activity in vitro namely, the DPPH, FRAP, and the LDL assay. The DPPH and FRAP assays are hydrophilic antioxidant assays and both demonstrate the ability of a putative antioxidant to donate electrons. The DPPH assay demonstrates the hydrogen donating ability of the putative antioxidants to stabilize ROS, the FRAP assay demonstrates the iron (III) reduction ability of putative antioxidants. The LDL assay is a hydrophobic antioxidant assay which demonstrates the ability of the putative antioxidant to inhibit lipid peroxidation caused by ROS.

Using the 2,2-Diphenyl-1-Picrylhydrazyl (DPPH) Radical to Assess the Antioxidant Ability of Polymer Compound 57

The DPPH assay is based on the change in absorbance at 515 nm, upon reduction of the DPPH radical, by an antioxidant. The antioxidant activity of a putative antioxidant is measured by monitoring the decrease in absorbance when the colour of the solution fades. In this assay, the reaction between the test antioxidant and DPPH radical is allowed to continue until it reaches a steady state. The amount of the radical quenched when steady state is reached is dependent on the antioxidant capacity and the concentration of the antioxidant.

100 µl (1 mg/3 ml) of the respective sample was added to 3.9 ml DPPH solution (25 mg/L in methanol). The decrease in absorbance at 515 nm was monitored using a Unicam UV-visible spectrophotometer, until the reaction reached steady state.

From the results in Table 3 below it can be seen that both hydroxytyrosol and the Polymer Compound 57 were found to be effective radical scavengers against the DPPH radical, with radical scavenging activities being compared to the standard ascorbic acid (100%).

TABLE 3

| Product | Radical Scavenging Activity (%) | Final time of reaction (min) |
| --- | --- | --- |
| Ascorbic acid (Std) (0.002M) | 100 | 4 |
| Hydroxytyrosol (0.002M) | 33.2 | 5 |
| Polymer Compound 57 (0.0004M) | 86.7 | 7 |

Using the FRAP Assay to Assess the Antioxidant Activity of Polymer Compound 57

The FRAP assay measures the ability of an antioxidant to reduce a ferroin analog, the Fe complex of tripyridyltriazine, Fe $(TPTZ)^{3+}$, to the intensely blue coloured $Fe^{2+}$ in an acidic medium. Results are obtained as absorbance increases at 593 nm and can be expressed relative to an antioxidant standard, ascorbic acid in this case.

1 ml (1 mg/3 ml) of the respective sample was added to 2.5 ml of potassium phosphate buffer (pH 7, 500 mM) 2.5 ml potassium ferricyanide was added. This was followed by incubation at 50° C. for 20 min. 10% (v/v) trichloracetic acid was added to stop the reaction. 2.5 ml of water was then added to 2.5 ml of the reaction. Iron chloride (0.5 ml) was added. The reaction was allowed to stand for 30 min after which the absorbance was read at 700 nm.

Polymer Compound 57 showed antioxidant activity equivalent 363 mg/L of ascorbic acid. An antioxidant activity almost equivalent to that of the substrates (hydroxytyrosol and ferulic acid) was achieved even though only a third of the concentration of the product was used compared to that of the substrate. The reducing properties of Polymer Compound 57 are associated with its free-radical chain breaking properties, initiated by it donating a hydrogen atom.

Using the (LDL) Assay to Assess the Antioxidant Activity of Antioxidants

Oxidation of low density lipoprotein (LDL) was performed according to the method developed by Nardini et al (1995). LDL was dialyzed in a 200 fold volume of PBS of pH 7 in the dark for 18 hrs. 100 µg/ml LDL, determined with the Bradford method, was oxidized with 5 µM $CuCl_2$ for 4 hrs at 37° C. in the presence and absence of 50 µM test antioxidant. Conjugated diene formation was measured spectroscopically at 234 nm using a Unicam UV-visible spectrophotometer.

The antioxidant ability of Polymer Compound 57 to inhibit LDL oxidation was assessed by adding it to a reaction mixture containing LDL previously treated with copper to initiate the oxidation. The antioxidant ability of the compound was measured based on the increase in absorbance due to diene conjugation at 234 nm.

Polymer Compound 57 showed an absorbance-decreasing effect and is thus able to prevent diene conjugation due to lipid peroxidation to varying degrees relative to the standard, ascorbic acid.

Lipid peroxidation results in the formation diene conjugation through a chain reaction of peroxidation. The two compounds are able to prevent this chain reaction and can be said to be chain breaking antioxidants.

Effect of Various Concentrations of Polymer Compound 57 on HaCaTs Cell Viability of Human Skin Cells (HaCaTs)

Ideally, to test the efficacy of an antioxidant the compound needs to be applied to a biological model involving cells. Keratinocytes (HaCaTs) were used as they are targets for most solar radiation-induced skin cancers and are exposed to numerous oxidants derived from normal metabolism, pathophysiological processes and extra cellular sources. To test the putative antioxidant activity of Polymer Compound 57, cells were exposed to UVA and the effects were measured (ie elevated ROS production, apoptotic proteins).

To evaluate the toxicity of Polymer Compound 57 an XTT assay was conducted. The assay is based on the ability of viable cells to reduce yellow XTT tetrazolium salts to an orange formazan which is then measured at an absorbance of 450 nm. The HaCaTs were incubated overnight with increasing concentrations of Polymer Compound 57. Cell viability was then evaluated by adding the XTT solution, incubating for 4 hrs at 37° C., and then reading the absorbance at 450 nm.

Concentrations higher than 1000 µM caused a marked decrease in cell viability. Polymer Compound 57 showed no negative effect on cell viability at concentrations of 200-500 µM, but concentrations higher than 500 µM resulted in marked decreases in cell viability.

To further explore the effect of the antioxidants a dose and time response study was carried out to determine the long term effect of Polymer Compound 57. HaCaTs cells were grown in the presence of the concentration ranges of Polymer Compound 57 which had been proved to be non-toxic to HaCaTs during the 24 hr incubation period as described in the previous paragraph. All the concentrations that proved non-toxic over a 24 hr period also proved to be non-toxic over a 3 day period. Over the 3 day period the cells displayed a standard sigmoidal cell growth curve indicative of no cell loss and these concentrations were used for all subsequent experiments.

ROS Assay to Elucidate the Effect Polymer Compound 57 on the Production of ROS Due to Irradiation UVA irradiation of cultured human skin cells results in over-elevated levels of $H_2O_2$ and other ROS (reactive oxygen species), with $H_2O_2$ being the predominant species. Dihydrorhodamine (DHR 123) can be used to detect $H_2O_2$ produced following irradiating the cells with UVA. It has been shown to react with $H_2O_2$ in the presence of peroxidase and is extensively used as a probe for the detection of intracellular $H_2O_2$. The mean fluorescence (MF), read on a fluorescent activated cell sorter (FACS) machine thus indicates intracellular $H_2O_2$ production. To elucidate the effect that Polymer Compound 57 would have on the over-expression of ROS due to irradiation, $H_2O_2$ production in keratinocytes was measured. The cells were first treated with the various concentrations of the Polymer Compound 57, irradiated with UVA and then exposed to the dye DHR 123.

The data showed that Polymer Compound 57 inhibited UVA-induced $H_2O_2$ production in a dose-dependent manner. The results indicate that Polymer Compound 57, at concentrations of 200 μM, reduced ROS levels to normal physiological levels of 87-100% mean fluorescent relative to the control of 100% mean fluorescent. At a concentration of 333 μM Polymer Compound 57 showed a ROS reduction effect with a mean fluorescence of 85%.

This result directly demonstrates that Polymer Compound 57 has potent radical scavenging activity which can prevent the over-production of intracellular $H_2O_2$ through a free radical scavenging pathway. This study suggests that the protective effect of Polymer Compound 57 against UV-induced ROS may take place through an interference with the reactions initiated by ROS. This interference might either be by directly neutralizing these intermediates (ROS), preventing formation of superoxide and/or hydrogen peroxide, or by regenerating the antioxidant system of the cells because UV irradiation is thought to deplete the antioxidants' involved in the defence of the cells.

Figure 7:
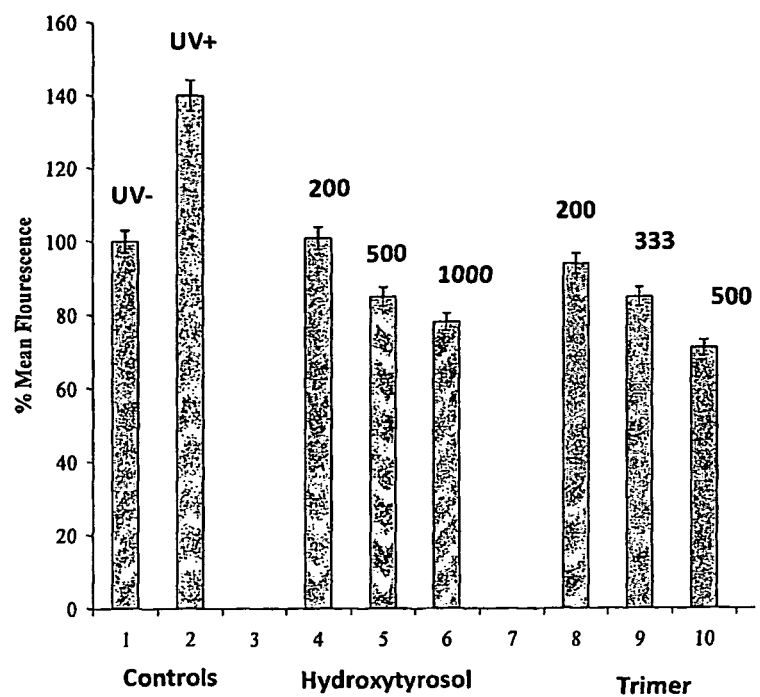
FIG. 7 is a bar graph depicting ROS assay results.

The results shown in FIG. 7 also indicate that there was an increase in the degree of ROS reduction correlating to an increase in the molecular weight of hydroxytyrosol and Polymer Compound 57 (respective MW 153 and 306). Thus it can be suggested that the effect of polymerization was an increase in antioxidant activity such that $H_2O_2$ levels were brought to normal physiological levels.

In summary, these tests show that Polymer Compound 57 is a potent protective agent for keratinocytes after UVA irradiation.

Evaluating the Effect of Polymer Compound 57 on UVA-Induced Apoptosis in HaCaTs Using Western Blot Analysis Apoptosis refers to a process of programmed cell death, which is considered a vital part of various processes including normal cell turnover, proper development, functioning of the immune system, chemical induced cell death and UVR overexposure. Necrosis is the alternative to apoptosis, and is considered a toxic process where the cell is a passive victim and follows an energy-independent mode of death. For present purposes apoptosis as a mode of cell death induced by UVA over-exposure was focussed on.

Apoptosis can take place through the extrinsic pathway or the intrinsic pathway. The extrinsic pathway involves transmembrane receptor-mediated interactions which involve members of the tumour necrosis factor (TNF). The intrinsic pathway is a mitochondrial-initiated event and thus is of interest for this study. The intrinsic pathway can progress in a caspase-dependent or independent way. The caspase-independent route involves a protein called AIF which when released from the mitochondria, translocates directly to the nucleus and induces apoptosis. The alternative caspase-dependent route involves members of the Bcl-2 family of proteins. This family of proteins is responsible for regulating the permeability of the mitochondrial membrane and can be either pro-apoptotic or anti-apoptotic; Bcl-2 is anti-apoptotic while Bax is pro-apoptotic. The cells' sensitivity to apoptotic stimuli depends on the balance of pro-apoptotic (Bax) and anti-apoptotic (Bcl-2) proteins. The ratio of these proteins seems to suggest the "apoptotic status" of the cell. An excess of Bax results in the cells being more susceptible to apoptosis, and an excess of Bcl-2 renders the cells more resistant to apoptosis. To determine the nature of the anti-apoptotic effect mediated by Polymer Compound 57 and hydroxytyrosol due to UVA irradiation, the Bax/Bcl-2 ratio was studied using Western blot analysis.

To evaluate the expression of Bcl-2, Bax and AIF, the cells were cultured and treated with varying concentrations between 200 and 1000 μM of Polymer Compound 57 and hydroxytyrosol for 18 hrs, and then irradiated at 22.3 J/cm². Protein extraction was conducted and proteins were quantified using the BCA method. Sham controls were included throughout and none were significantly different from non-UV irradiated controls. The purpose of this control is to ensure that it is only the UVA rays that result in the observed effects, and not the heat in the chamber. Alpha tubulin was used as a loading control in each experiment to ensure that the results were quantified correctly. Since the Western blot results are quantified by band size, it is important to ensure that each sample has the same amount of protein when loaded and the loading control helps to determine this. The band obtained when the proteins are probed with the loading control represent the amount of protein in that loaded sample. The results of Western blot analysis showed that the two compounds considerably reduced the expression of Bax (FIG. 8.1, 8.4) AIF (FIG. 8.3, 8.6) and induce the over-expression of Bcl-2 (FIG. 8.2, 8.5) in a concentration dependent manner. It should be noted that UV+ and UV− do not always occur in the same order as they were sometimes loaded differently.

Evaluating the Effect of Hydroxytyrosol and Polymer Compound 57 on UVA-Induced Apoptosis in HaCaTs Using Western Blot Analysis Hydroxytyrosol at a concentration of 1000 μM showed the greatest decrease in Bax expression by bringing Bax levels to the same expression levels as the control (FIG. 8.1). Polymer Compound 57 at a concentration of 200 μM reduced Bax levels by 75%, while the other two concentrations tested (333 and 500 μM) reduced Bax levels by 87.5% relative the control (FIG. 8.4).

Hydroxytyrosol at a concentration of 200 μM brought AIF levels of expression to normal levels in relation to the control. At the highest concentration (1000 μM), hydroxytyrosol reduced AIF levels by 15% relative to the control (FIG. 8.3). Polymer Compound 57 reduced AIF levels in a concentration dependent manner, to 28% for the 200 μM, and 32% for concentrations 333 and 500 μM, relative to the control (FIG. 8.6).

The presence of hydroxytyrosol caused an increase in Bcl-2 expression in a concentration-dependent manner. Concentrations 200 and 500 μM brought Bcl-2 expression to normal levels of expression relative to the control. The highest concentration, 1000 μM, lead to an increase in Bcl-2 levels of expression of 7% relative to the control as shown in FIG. 8.2. Polymer Compound 57 increased Bcl-2 levels in a concentration-dependent manner; the highest concentration (500 μM) increased Bcl-2 levels by 16% relative to the control (FIG. 8.5). It is suggested that the antioxidative compounds passively diffused into the cells, thereby provoking anti-apoptotic intracellular signals. The fact that the compounds affected the proteins of the Bcl-2 gene family in pre-treated, UVA irradiated cells suggests that these compounds inhibit apoptosis due to irradiation by inhibiting the intrinsic pathway of apoptosis. The results suggest a possible mechanism in which Bcl-2 over-expression, due to the antioxidants, stabilize the mitochondrial functions and block the release of cytochrome c by increasing the antioxidant capacity of the cells. Recent evidence suggests that Bcl-2 can also guard other organelles by fortifying the cellular antioxidant defence. This was clearly the case in the UVA-induced antioxidant treated cells, where Bcl-2 over-expression due to pre-treatment with the antioxidants prevented mitochondrial membrane depolarization as the compounds were able to reduce Bax levels of expression (decreased mitochondrial membrane permeability) AIF and ROS formation.

Comparison of Different Concentrations of Hydroxytyrosol and Polymer Compound 57 on Protein Expression As shown in Table 4 and FIGS. 9.1 to 9.3, the highest concentrations of hydroxytyrosol and Polymer Compound 57 were most effective in reducing Bax and AIF levels and in inducing over expression of Bcl-2.

The highest tested concentration of hydroxytyrosol, 1000 µM, caused the greatest reduction in Bax levels of expression relative to the control (100%), by bringing expression levels to 100%, which is a normal physiological level of expression relative to the control in this experiment. Polymer Compound 57 showed the greatest reduction in Bax levels at its lowest tested concentration, 200 µM. The Bax levels were 70% lower than that of the control (100%). The lowest concentration of Polymer Compound 57 decreased Bax levels by 85% relative to the control (100%). It can thus be concluded that Polymer Compound 57 showed greater antioxidant activity than the substrate, hydroxytyrosol.

Similarly, for hydroxytyrosol, the concentration that had the greatest effect on inducing Bcl-2 levels was 1000 µM and for Polymer Compound 57 it was 500 µM as shown in Table 4 and FIG. 9.2.

TABLE 4

| | Concentrations (µM) | | | | | |
| --- | --- | --- | --- | --- | --- | --- |
| | Hydroxytyrosol | | | Polymer Compound 57 | | |
| | 200 | 333 | 1000 | 200 | 333 | 1000 |
| % Bax Expression | 128 | 116 | 100 | 31 | 17 | 14 |
| % Bcl-2 Expression | 83 | 90 | 110 | 50 | 84 | 118 |
| % AIF Expression | 91 | 82 | 42 | 78 | 74 | 38 |

Overall Assessment of Antioxidant Activities of Hydroxytyrosol and Polymer Compound 57

Polymer Compound 57 showed stronger antioxidant activity than its precursor, hydroxytyrosol, as it was observed to induce greater levels of over-expression of Bcl-2, and decreased the over-expression of AIF and Bax.

Antioxidants are extensively metabolized in vivo, resulting in metabolized forms of the parent antioxidant. The eventual antioxidant effect of these metabolites could result in increased antioxidant activity or decreased antioxidant activity as compared with the original antioxidant. The in vitro antioxidant assays, DPPH, FRAP and LDL all showed Polymer Compound 57 to have the highest antioxidant activity. The same trend was observed in the UVA study with HaCaTs cells where the polymeric product was found to have better antioxidant activity than the monomer hydroxytyrosol. This suggests that the metabolism did not have an effect on the antioxidant activity of these compounds by altering the chemistry of the parent compound, and further, it suggests that the metabolites formed worked synergistically with the parent compound to be able to reduce cytotoxicity of UV radiation.

Use of Hydroxytyrosol Polymers

The antioxidant properties of the hydroxytyrosol polymers, particularly the dimer, trimer and higher oligomers, make them highly suited to use in UV protectant compositions, particularly topically applied products. These include creams, lotions and the like intended for use on skin as cosmetics and sun tanning preparations. Typically the selected polymer, or group of polymers, will be used in such preparations in a concentration range of 5-15 mM.

A typical preparation may include, in addition to the polymer, water, cetostearyl alcohol, liquid and white soft paraffin (to enhance absorption), sodium lauryl sulphate or sodium docdecyl sulphate (both of these are detergent based to help with lipid absorption as the cells of the skin have lipid membranes) and a preservative such as phenoxyethanol. Clearly, any suitable preparation can be used.

It is further proposed to use the polymers as an antioxidant active ingredient in medicaments. These may include any other suitable active ingredients and excipients and may be in the form of parenterals or non-parenterals, particularly tablets and capsules.

It is expected that one or more of the polymers will exhibit enhanced activity over the others and these will preferably be used in the preparations or medicaments.

It will be appreciated that other processes for the preparation of a hydroxytyrosol polymer exist which fall within the scope of the invention. For example, the reaction medium may contain water-miscible organic solvents such as acetone, methanol or ethanol, or water-immiscible solvents such as ethyl acetate, at percentages (volume for volume) ranging from 10% to 70% with aqueous buffer. Also, the range of substrate concentration ratios (relative to the amount of laccase present) may vary from 50 U laccase:1 g hydroxytyrosol to 1000 U laccase: 1 g hydroxytyrosol, and laccase may be used in a free or immobilised form.

The invention claimed is:

1. A hydroxytyrosol polymer, having the structure:

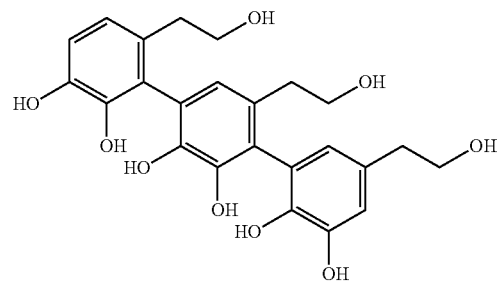 [SMILES: OCCc1cc(O)c(O)c(-c2c(CCO)cc(-c3c(CCO)ccc(O)c3O)c(O)c2O)c1]

formed by C—C coupling of hydroxytyrosol.

2. An antioxidant composition which comprises a hydroxytyrosol polymer having the structure:

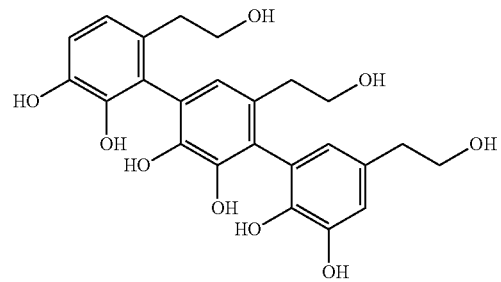 [SMILES: OCCc1cc(O)c(O)c(-c2c(CCO)cc(-c3c(CCO)ccc(O)c3O)c(O)c2O)c1]

formed by C—C coupling of hydroxytyrosol.

3. The antioxidant composition as claimed in claim 2 which is suitable for use on human or animal skin.

4. The antioxidant composition as claimed in claim 2 in the form of a cream, lotion or spray.

5. A process for preparing a hydroxytyrosol polymer which comprises polymerizing hydroxytyrosol using laccase as a catalyst to form a hydroxytyrosol polymer, having the structure:

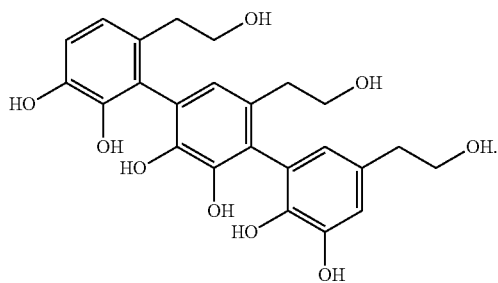 [SMILES: OCCc1cc(O)c(O)c(-c2c(CCO)cc(-c3c(CCO)ccc(O)c3O)c(O)c2O)c1]

6. A method for protecting the skin of a subject from UV irradiation, the method comprising applying an effective amount of a hydroxytyrosol polymer having the structure:

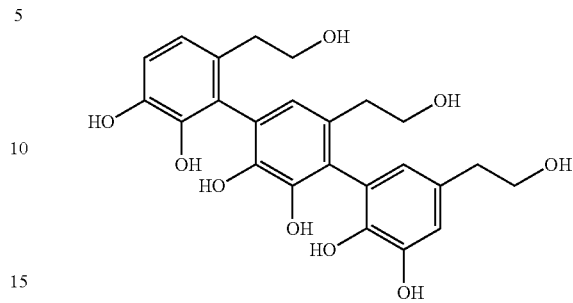

formed by C—C coupling of hydroxytyrosol to the skin of the subject.

* * * * *